United States Patent
Onuma

(10) Patent No.: US 9,044,576 B2
(45) Date of Patent: *Jun. 2, 2015

(54) CATHETER WITH VALVE

(71) Applicant: Covidien LP, Mansfield, MA (US)

(72) Inventor: Tadatsugu Onuma, Shizuoka-ken (JP)

(73) Assignee: Covidien LP, Mansfield, MA (US)

( * ) Notice: Subject to any disclaimer, the term of this patent is extended or adjusted under 35 U.S.C. 154(b) by 115 days.

This patent is subject to a terminal disclaimer.

(21) Appl. No.: 13/738,174

(22) Filed: Jan. 10, 2013

(65) Prior Publication Data

US 2014/0025019 A1    Jan. 23, 2014

Related U.S. Application Data

(63) Continuation of application No. 12/463,019, filed on May 8, 2009, now Pat. No. 8,864,724.

(30) Foreign Application Priority Data

May 14, 2008    (JP) .................................. 2008-126661

(51) Int. Cl.
*A61M 25/14*    (2006.01)
*A61M 25/00*    (2006.01)
(Continued)

(52) U.S. Cl.
CPC ... *A61M 25/0075* (2013.01); *A61M 2025/0078* (2013.01); *A61M 2039/027* (2013.01); *A61M 2039/2433* (2013.01)

(58) Field of Classification Search
CPC ..................... A61M 25/0021; A61M 25/0075; A61M 25/0054; A61M 25/003; A61M 25/0032; A61M 25/01; A61M 25/0102

USPC .................. 604/246, 247, 96.01, 164.01, 523
See application file for complete search history.

(56) References Cited

U.S. PATENT DOCUMENTS

| | | |
|---|---|---|
| 4,391,276 A | 7/1983 | Lazarus et al. |
| 4,403,983 A | 9/1983 | Edelman et al. |
| 4,475,898 A | 10/1984 | Brodner et al. |

(Continued)

FOREIGN PATENT DOCUMENTS

| | | |
|---|---|---|
| EP | 0 299 622 | 1/1989 |
| EP | 0 554 722 | 8/1993 |

(Continued)

OTHER PUBLICATIONS

Office Action from Chinese Appl. No. 200910204452.0 dated Sep. 27, 2013.

(Continued)

*Primary Examiner* — Bhisma Mehta
*Assistant Examiner* — William Frehe
(74) *Attorney, Agent, or Firm* — John Paul Mello, Esq.

(57) ABSTRACT

A catheter including one or more bidirectional valves is provided. The catheter includes a tubular body having proximal and distal ends, and inner and outer surfaces, and at least one valve formed near the distal end of the tubular body. The valve includes a deformation portion that defines a slit that is openable and closable. The openable/closable slit communicates from the inner surface to the outer surface of the tubular body, wherein the distance between the inner surface and the outer surface of the tubular body progressively becomes thinner approaching the openable/closable slit within the deformation portion.

14 Claims, 3 Drawing Sheets

(51) Int. Cl.
    *A61M 39/02*      (2006.01)
    *A61M 39/24*      (2006.01)

(56) References Cited

U.S. PATENT DOCUMENTS

| | | |
|---|---|---|
| 4,493,696 A | 1/1985 | Uldall |
| 4,549,879 A | 10/1985 | Groshong et al. |
| 4,568,329 A | 2/1986 | Mahurkar |
| 4,583,968 A | 4/1986 | Mahurkar |
| 4,619,643 A | 10/1986 | Bai |
| 4,626,240 A | 12/1986 | Edelman et al. |
| 4,643,711 A | 2/1987 | Bates |
| 4,671,796 A | 6/1987 | Groshong et al. |
| 4,692,141 A | 9/1987 | Mahurkar |
| 4,701,166 A | 10/1987 | Groshong et al. |
| 4,737,152 A | 4/1988 | Alchas |
| 4,753,640 A | 6/1988 | Nichols et al. |
| 4,769,005 A | 9/1988 | Ginsburg et al. |
| 4,772,268 A | 9/1988 | Bates |
| 4,772,269 A | 9/1988 | Twardowski et al. |
| 4,795,439 A | 1/1989 | Guest |
| 4,808,155 A | 2/1989 | Mahurkar |
| 4,808,156 A | 2/1989 | Dean |
| 4,813,934 A | 3/1989 | Engelson et al. |
| 4,842,582 A | 6/1989 | Mahurkar |
| 4,895,561 A | 1/1990 | Mahurkar |
| 4,897,079 A | 1/1990 | Zaleski et al. |
| 4,961,809 A | 10/1990 | Martin |
| 4,973,319 A | 11/1990 | Melsky |
| 4,995,863 A | 2/1991 | Nichols et al. |
| 4,995,865 A | 2/1991 | Gahara et al. |
| 5,009,636 A | 4/1991 | Wortley et al. |
| 5,035,399 A | 7/1991 | Rantanen-Lee |
| 5,041,083 A | 8/1991 | Tsuchida et al. |
| 5,053,004 A | 10/1991 | Markel et al. |
| 5,053,023 A | 10/1991 | Martin |
| 5,057,073 A | 10/1991 | Martin |
| 5,059,170 A | 10/1991 | Cameron |
| 5,085,632 A | 2/1992 | Ikada et al. |
| 5,106,368 A | 4/1992 | Uldall et al. |
| 5,112,301 A | 5/1992 | Fenton, Jr. et al. |
| 5,135,599 A | 8/1992 | Martin et al. |
| 5,147,332 A | 9/1992 | Moorehead |
| 5,156,592 A | 10/1992 | Martin et al. |
| 5,160,325 A | 11/1992 | Nichols et al. |
| 5,163,921 A | 11/1992 | Feiring |
| 5,167,623 A | 12/1992 | Cianci et al. |
| 5,171,218 A | 12/1992 | Fonger et al. |
| 5,188,593 A | 2/1993 | Martin |
| 5,190,520 A | 3/1993 | Fenton, Jr. et al. |
| 5,195,962 A | 3/1993 | Martin et al. |
| 5,197,951 A | 3/1993 | Mahurkar |
| 5,209,723 A | 5/1993 | Twardowski et al. |
| 5,219,335 A | 6/1993 | Willard et al. |
| 5,221,255 A | 6/1993 | Mahurkar et al. |
| 5,221,256 A | 6/1993 | Mahurkar |
| 5,224,938 A | 7/1993 | Fenton, Jr. |
| 5,250,034 A | 10/1993 | Appling et al. |
| 5,261,885 A | 11/1993 | Lui |
| 5,267,979 A | 12/1993 | Appling et al. |
| 5,269,768 A | 12/1993 | Cheung |
| 5,304,155 A | 4/1994 | Lui |
| 5,308,338 A | 5/1994 | Helfrich |
| 5,346,471 A | 9/1994 | Raulerson |
| 5,348,536 A | 9/1994 | Young et al. |
| 5,360,397 A | 11/1994 | Pinchuk |
| 5,364,344 A | 11/1994 | Beattie et al. |
| 5,374,245 A | 12/1994 | Mahurkar |
| 5,378,230 A | 1/1995 | Mahurkar |
| 5,380,276 A | 1/1995 | Miller et al. |
| 5,395,316 A | 3/1995 | Martin |
| 5,399,172 A | 3/1995 | Martin et al. |
| 5,403,291 A | 4/1995 | Abrahamson |
| 5,405,341 A | 4/1995 | Martin |
| 5,451,206 A | 9/1995 | Young |
| 5,464,398 A | 11/1995 | Haindl |
| 5,472,417 A | 12/1995 | Martin et al. |
| 5,480,380 A | 1/1996 | Martin |
| 5,486,159 A | 1/1996 | Mahurkar |
| 5,489,278 A | 2/1996 | Abrahamson |
| 5,509,897 A | 4/1996 | Twardowski et al. |
| 5,522,807 A | 6/1996 | Luther |
| 5,531,679 A | 7/1996 | Schulman et al. |
| 5,554,136 A | 9/1996 | Luther |
| 5,556,390 A | 9/1996 | Hicks |
| 5,569,182 A | 10/1996 | Twardowski et al. |
| 5,571,093 A | 11/1996 | Cruz et al. |
| D381,420 S | 7/1997 | Musgrave et al. |
| D384,411 S | 9/1997 | Musgrave et al. |
| D384,741 S | 10/1997 | Musgrave et al. |
| 5,683,640 A | 11/1997 | Miller et al. |
| 5,685,867 A | 11/1997 | Twardowski et al. |
| 5,702,365 A | 12/1997 | King |
| 5,718,678 A | 2/1998 | Fleming, III |
| 5,776,096 A | 7/1998 | Fields |
| 5,797,869 A | 8/1998 | Martin et al. |
| 5,807,311 A | 9/1998 | Palestrant |
| 5,807,329 A | 9/1998 | Gelman |
| 5,807,349 A | 9/1998 | Person et al. |
| 5,810,789 A | 9/1998 | Powers et al. |
| 5,830,184 A | 11/1998 | Basta |
| 5,830,196 A | 11/1998 | Hicks |
| 5,868,717 A | 2/1999 | Prosl |
| 5,928,203 A | 7/1999 | Davey et al. |
| 5,947,953 A | 9/1999 | Ash et al. |
| 5,961,485 A | 10/1999 | Martin |
| 5,961,486 A | 10/1999 | Twardowski et al. |
| 5,968,009 A | 10/1999 | Siman |
| 5,976,103 A | 11/1999 | Martin |
| 5,984,903 A | 11/1999 | Nadal |
| 5,989,206 A | 11/1999 | Prosl et al. |
| 5,989,213 A | 11/1999 | Maginot |
| 5,993,437 A | 11/1999 | Raoz |
| 6,001,079 A | 12/1999 | Pourchez |
| 6,004,310 A | 12/1999 | Bardsley et al. |
| 6,099,519 A | 8/2000 | Olsen et al. |
| 6,123,725 A | 9/2000 | Aboul-Hosn |
| 6,126,631 A | 10/2000 | Loggie |
| 6,146,354 A | 11/2000 | Beil |
| 6,156,016 A | 12/2000 | Maginot |
| 6,190,349 B1 | 2/2001 | Ash et al. |
| 6,190,371 B1 | 2/2001 | Maginot et al. |
| 6,206,849 B1 | 3/2001 | Martin et al. |
| 6,273,875 B1 | 8/2001 | Siman et al. |
| 6,280,423 B1 | 8/2001 | Davey et al. |
| 6,293,927 B1 | 9/2001 | McGuckin, Jr. |
| 6,342,120 B1 | 1/2002 | Basta |
| 6,346,090 B1 | 2/2002 | Liska et al. |
| 6,394,141 B2 | 5/2002 | Wages et al. |
| 6,409,700 B1 | 6/2002 | Siegel, Jr. et al. |
| 6,447,488 B2 | 9/2002 | Estabrook et al. |
| 6,461,321 B1 | 10/2002 | Quinn |
| 6,475,207 B1 | 11/2002 | Maginot et al. |
| 6,482,169 B1 | 11/2002 | Kuhle |
| 6,506,182 B2 | 1/2003 | Estabrook et al. |
| 6,569,145 B1 | 5/2003 | Shmulewitz et al. |
| 6,579,261 B1 | 6/2003 | Kawamura |
| 6,585,705 B1 | 7/2003 | Maginot et al. |
| 6,592,542 B2 | 7/2003 | Childers et al. |
| 6,592,558 B2 | 7/2003 | Quah |
| 6,595,966 B2 | 7/2003 | Davey et al. |
| 6,620,118 B1 | 9/2003 | Prosl et al. |
| 6,638,242 B2 | 10/2003 | Wilson et al. |
| 6,692,473 B2 | 2/2004 | St. Cyr et al. |
| 6,695,832 B2 | 2/2004 | Schon et al. |
| 6,719,749 B1 | 4/2004 | Schweikert et al. |
| 6,723,075 B2 | 4/2004 | Davey et al. |
| 6,723,084 B1 | 4/2004 | Maginot et al. |
| 6,730,096 B2 | 5/2004 | Basta |
| 6,743,218 B2 | 6/2004 | Maginot et al. |
| 6,749,580 B2 | 6/2004 | Work et al. |
| 6,758,836 B2 | 7/2004 | Zawacki |
| 6,786,884 B1 | 9/2004 | DeCant, Jr. et al. |
| 6,808,510 B1 | 10/2004 | DiFiore |

(56) References Cited

U.S. PATENT DOCUMENTS

| | | |
|---|---|---|
| 6,814,718 B2 | 11/2004 | McGuckin, Jr. et al. |
| 6,858,019 B2 | 2/2005 | McGuckin, Jr. et al. |
| 6,872,198 B1 | 3/2005 | Wilson et al. |
| 6,911,014 B2 | 6/2005 | Wentling et al. |
| 6,921,396 B1 | 7/2005 | Wilson et al. |
| 6,942,635 B2 | 9/2005 | Rosenblatt et al. |
| 6,942,653 B2 | 9/2005 | Quinn |
| 6,966,886 B2 | 11/2005 | Appling |
| 6,969,381 B2 | 11/2005 | Voorhees |
| 6,976,973 B1 | 12/2005 | Ruddell et al. |
| 6,986,752 B2 | 1/2006 | McGuckin, Jr. et al. |
| 6,991,625 B1 | 1/2006 | Gately et al. |
| 7,008,395 B1 | 3/2006 | Loggie |
| 7,008,412 B2 | 3/2006 | Maginot |
| 7,011,645 B2 | 3/2006 | McGuckin, Jr. et al. |
| 7,013,928 B2 | 3/2006 | Navis |
| 7,048,680 B2 | 5/2006 | Viole et al. |
| 7,066,914 B2 | 6/2006 | Andersen |
| 7,077,829 B2 | 7/2006 | McGuckin, Jr. et al. |
| 7,413,564 B2 | 8/2008 | Morris et al. |
| 7,491,192 B2 | 2/2009 | DiFiore |
| 2002/0121282 A1 | 9/2002 | McGuckin, Jr. et al. |
| 2002/0156430 A1 | 10/2002 | Haarala et al. |
| 2003/0032918 A1 | 2/2003 | Quinn |
| 2003/0093029 A1 | 5/2003 | McGuckin, Jr. et al. |
| 2003/0191425 A1 | 10/2003 | Rosenblatt |
| 2004/0249337 A1 | 12/2004 | DiFiore |
| 2005/0033222 A1 | 2/2005 | Haggstrom et al. |
| 2005/0043703 A1 | 2/2005 | Nordgren |
| 2005/0085765 A1 | 4/2005 | Voorhees |
| 2005/0090776 A1 | 4/2005 | McGuckin, Jr. et al. |
| 2005/0215978 A1 | 9/2005 | Ash |
| 2005/0228339 A1 | 10/2005 | Clark |
| 2005/0256509 A1 | 11/2005 | Sakai |
| 2005/0267400 A1 | 12/2005 | Haarala et al. |
| 2005/0288623 A1 | 12/2005 | Hjalmarsson |
| 2006/0004325 A1 | 1/2006 | Hamatake et al. |
| 2006/0149191 A1 | 7/2006 | DiFiore |
| 2006/0253063 A1 | 11/2006 | Schweikert |
| 2007/0100298 A1 | 5/2007 | Appling |
| 2007/0219527 A1 | 9/2007 | Barron |
| 2007/0225678 A1 | 9/2007 | Lui |
| 2009/0054825 A1 | 2/2009 | Melsheimer et al. |
| 2009/0312718 A1 | 12/2009 | Onuma |
| 2010/0069818 A1 | 3/2010 | Smouse |
| 2010/0081986 A1 | 4/2010 | Matson |
| 2011/0130745 A1 | 6/2011 | Shevgoor et al. |

FOREIGN PATENT DOCUMENTS

| | | |
|---|---|---|
| EP | 0 322 225 | 2/1995 |
| EP | 0 713 406 | 3/1998 |
| EP | 0864336 | 9/1998 |
| EP | 0 864 336 | 3/1999 |
| EP | 0 570 530 131 | 8/1999 |
| EP | 0 555 780 B1 | 9/1999 |
| EP | 1595565 | 11/2005 |
| EP | 1 144 039 B1 | 12/2005 |
| EP | 207-175297 | 7/2007 |
| EP | 1955728 A1 | 8/2008 |
| EP | 2 168 625 | 3/2010 |
| JP | 2001518324 | 10/2001 |
| JP | 2005323813 | 11/2005 |
| WO | 92/22342 A1 | 12/1992 |
| WO | WO 95/04567 | 2/1995 |
| WO | WO 97/37699 | 10/1997 |
| WO | WO 98/41277 | 9/1998 |
| WO | WO 99/38550 | 8/1999 |
| WO | WO 99/65557 | 12/1999 |
| WO | WO 00/06239 | 2/2000 |
| WO | 00/56387 A1 | 9/2000 |
| WO | WO 01/91845 | 12/2001 |
| WO | WO 02/13899 | 2/2002 |
| WO | WO 02/18004 | 3/2002 |
| WO | WO 03/033049 | 4/2003 |
| WO | WO 03/066148 | 8/2003 |
| WO | WO 2004/093956 | 11/2004 |
| WO | WO 2005/023336 | 3/2005 |
| WO | WO 2005/077449 | 8/2005 |
| WO | WO 2005/084741 | 9/2005 |
| WO | WO 2006/014339 | 2/2006 |
| WO | 2006/122026 A2 | 11/2006 |

OTHER PUBLICATIONS

EP Search Report from EP Application No. EP 12 18 4656 dated May 11, 2012.

Extended European Search Report corresponding to EP Application No. 09 17 0662, completed Jan. 11, 2010; mailed Jan. 27, 2010 (7 pages).

Extended European Search Report issued by the European Patent Office and completed on Sep. 22, 2009 in co-pending European Paten Application No. EP 09251289.6.

Office Action issued in Japanese Application No. 2013-137993 mailed May 1, 2014.

CATHETER WITH VALVE

CROSS REFERENCE TO RELATED APPLICATIONS

The present application is a continuation application of U.S. patent application Ser. No. 12/463,019, filed May 8, 2009, the entire contents of which are incorporated herein by reference.

TECHNICAL FIELD

The present invention relates to a catheter with one or more valves capable of passing a liquid from the interior to the exterior of the catheter or passing a liquid from the exterior to the interior of the catheter via the one or more valves.

BACKGROUND

Catheters have been placed in the body of a patient and used to supply anticancer agents, nutritional formulations, or other such items into a patient's vein either temporarily or on a long-term basis. To infuse a stabilized drug solution with the use of a catheter in this fashion, it is important that infection and complications be prevented, that the catheter not break or move, and that the catheter also does not become occluded. However, when a catheter with an open tip is used, blood sometimes enters the catheter, coagulates, and the catheter becomes occluded. To prevent occlusion of catheters from such blood coagulation, the interior space of the catheter is generally filled with physiological saline including added heparin; however, this practice is problematic in that it complicates procedures when a catheter is placed in the body of a patient and represents a burden on health care providers and patients.

Consequently, a catheter including a valve able to prevent occlusion of the catheter due to coagulation of blood has been developed (e.g., see Japanese Unexamined Patent Application Publication S60-58167) by eliminating the tip opening and providing a valve which is normally closed and opens only at times such as when a drug solution is infused between the inside and the outside of the catheter or when blood is collected. Such a catheter with valve (bidirectional valve) is made from an elastic, plastic material, the tip is closed, and at the tip there is formed a linear slit. As a result, when a predetermined pressure differential develops between the inside and outside of such a catheter with valve, the slit opens, and a drug solution can be infused into a vein, or blood within a vein can be released into the catheter and collected. When a predetermined pressure differential between the inside and outside of a catheter with the valve has not developed, the slit is closed, and there is consequently no coagulation of blood within the slit.

Nonetheless, when a drug solution flows from the inside to the outside of a conventional catheter with valve described above, the slit closes with comparative ease, but a problem exists in that when blood flows from outside toward the inside of the catheter with the valve, the opposing surfaces which form the slit are subject to contact pressure, and it is difficult for the slit to open.

Therefore, it would be beneficial to have a catheter with a valve capable of providing a smooth the flow of a liquid both when a liquid flows from the inside toward the outside of the catheter, and when a liquid flows from the outside toward the inside of the catheter.

SUMMARY

Accordingly, a catheter with one or more bidirectional valves is provided. The catheter includes a tubular body endowed with elasticity and plasticity and the tip of which is closed, and in which a valve passing from the inside surface to the outside surface of the tubular body and provided with a slit able to open and close is formed at the tip of the tubular body. The outer circumferential portion of the slit in the valve includes a bidirectional deformation part which, when a liquid passes via the valve from the interior to the exterior of the tubular body, or when a liquid passes via the valve from the exterior to the interior of the tubular body, is easily deformed by the pressure of a liquid toward either the outside or the inside of the tubular body and opens the slit.

The outer circumferential portion of the slit includes a bidirectional deformation part which is easily deformed by the pressure of a liquid toward either the outside or the inside of the tubular body and opens the slit. As a result, the slit is made to open easily not only when a liquid flows from the inside toward the outside, but also when a liquid flows from the outside toward the inside of the catheter with valve, and the flow of a liquid in both inward and outward directions can be made smooth. Additionally, when the pressure differential between the inside and the outside of the catheter with valve is small, the slit is maintained in a closed status by the elasticity of the bidirectional deformation part.

The slit may be formed so as to extend along the axial direction of the catheter with valve, but the slit may also be extended in a direction oblique to the axial direction of the catheter with valve, or extended so as to be perpendicular thereto. The tubular body may be formed in a circular tube shape, and the bidirectional deformation part may be provided by creating a shape differing from other portions formed in the circular tube shape of the catheter with valve or by making the deformation part more flexible than other parts of the catheter. The liquid pertaining to the present disclosure is, for example, an anticancer agent, nutritional agent, or other such drug solution; blood or the like; or a liquid in infused into a vein or taken from a vein of a patient, and hereinafter, a liquid flowing from the inside toward the outside of the catheter with valve is described as a drug solution, and a liquid flowing from the outside toward the inside of the catheter with valve is described as blood.

In an alternative embodiment, bidirectional deformation part and the outer circumferential portion of the slit are provided by being made to project to the inside of the tubular body. As a result, when blood flows from the outside to the inside of the catheter with valve due to blood collection or checking for regurgitation, the blood places pressure on the bidirectional deformation part from a recessed surface side, and the slit opens easily. As a result, the flow of blood from the outside toward the inside of the catheter with valve is made smooth. When a drug solution flows from the inside toward the outside of the catheter with valve to supply said solution to the vein of a patient, the drug solution places pressure on the bidirectional deformation part from a projecting surface side, but in such case, infusion of the drug solution is performed by use of an injection syringe or supply device.

In another embodiment, the bidirectional deformation part is provided by making the outer circumferential portion of the slit thin-walled. As a result, the bidirectional deformation part is easily deformed for the fact of being made thin-walled, and when a drug solution flows from the inside toward the outside, or when blood flows from the outside toward the inside of the catheter with valve, in either case, the slit opens easily, and the flow of drug solution or blood toward its respective direction of orientation can be made smooth. In this instance, the thin-walled bidirectional deformation part may be provided by forming oblique surfaces such that the sides of the slit gradually become thin-walled; by forming a groove-shaped, thin-walled portion at a part maintaining a predetermined interval from the slit; or by making the entire part thin-walled.

When a thin-walled bidirectional deformation part is provided by forming oblique surfaces, opposing surfaces trapping and confronting the slit in the catheter with valve are provided with a required contact width for closing the slit when the pressure differential between the inside and outside of the catheter with valve is below a predetermined level. The oblique surfaces and groove-shaped, thin-walled part may also be provided at the inner circumference or outer circumference of the bidirectional deformation part, or at both the inner circumference and outer circumference.

In yet another embodiment, the bidirectional deformation part is provided by forming oblique surfaces on the outer circumference or inner circumference of parts opposed across the slit in the tubular shape, such that the slit side gradually becomes thin-walled. As a result of this configuration, when a drug solution flows from the inside toward the outside, or when blood flows from the outside toward the inside of the catheter with valve, in either case, the slit opens easily, and the flow of drug solution or blood toward its respective direction of orientation can be made smooth. In this instance, when an oblique surface is formed at the outer circumference, and blood thereby flows from the outside toward the inside of the catheter with valve, the slit opens more easily, and when an oblique surface is formed at the inner circumference, and a drug solution thereby flows from the inside toward the outside of the catheter with valve, the slit opens more easily. In these instances too, opposing surfaces trapping and confronting the slit in the catheter with valve are provided with a required contact width for closing the slit when the pressure differential between the inside and outside of the catheter with valve is below a predetermined level.

In still another embodiment, a plurality of valves provided with a slit and a bidirectional deformation part is formed. As a result, the provision of a plurality of valves allows more reliable inflow of drug solution or outflow of blood through the valve. For example, even if one valve is clogged, infusion of drug solution or outflow of blood can be accomplished through other valves. The plurality of valves in this instance may include an identical item or different items.

In still yet another embodiment, the plurality of bidirectional deformation parts provided with a plurality of valves includes a bidirectional deformation part provided by forming an oblique surface such that a predetermined slit side at the outer circumference of confronting portions across a predetermined slit among a plurality of slits forms an oblique surface that gradually becomes thin-walled, and a bidirectional deformation part provided by forming an oblique surface such that another slit side at the inner circumference of confronting portions across another slit among the plurality of slits forms an oblique surface that gradually becomes thin-walled.

As a result, when blood flows from the outside toward the inside of the catheter, a bidirectional deformation part provided by forming an oblique surface at the outer circumference is easily deformed at the inner circumference, and when a drug solution flows from the inside toward the outside of the catheter with valve, a bidirectional deformation part provided by forming an oblique surface at the inner circumference is easily deformed at the outer circumference. When a drug solution flows from the inside toward the outside of the catheter, and when blood flows from the outside toward the inside of the catheter with valve, in both cases, the flow of drug solution or blood can be made smooth.

DETAILED DESCRIPTION

Figure 1:
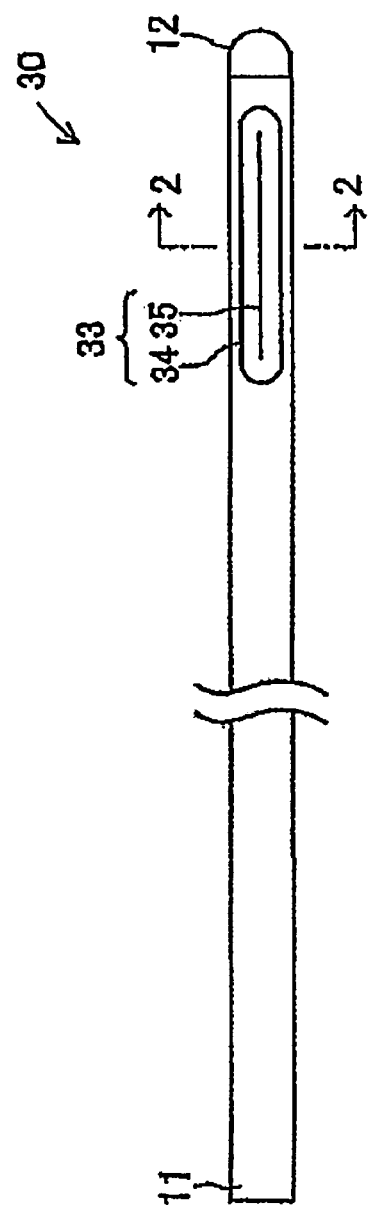
FIG. 1 is a planar view illustrating a catheter according to an embodiment of the present disclosure.
Figure 2:
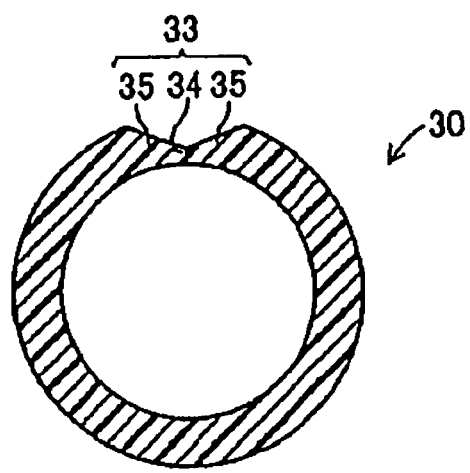
FIG. 2 is a cross-sectional view of 2-2 in FIG. 1.

Catheters according to embodiments of the present disclosure are described in detail hereafter with the use of drawings. FIGS. 1 and 2 illustrate a first embodiment of a catheter with valve shown generally as catheter 30. Catheter 30 is used to supply an anticancer agent, nutritional agent, or other such drug solution into a vein (e.g., B1-B3) of a patient A (see FIG. 3). A port 17 is connected to a base terminal 11 before catheter 30 is placed in the vein of the patient A. Catheter 30 includes a long, thin tubular body made from a flexible polyurethane resin and endowed with elasticity and plasticity. A dome-shaped wall portion 12 is formed at the tip of the catheter 30, and the tip of catheter 30 is closed by this wall portion 12. Wall portion 12 is made from a polyurethane or silicone softer than the body of catheter 30 and is attached to the body of catheter 30 by adhesion or deposition.

A valve 33 with a long, thin elliptical shape in planar view (attitude in FIG. 1) along the axial direction (lengthwise direction) of the catheter 30 is formed at an area of the catheter 30 more toward the base terminal 11 than the wall portion 12 on the circumferential surface of the catheter 30. Valve 33 includes a linear slit 34 extending along the axial direction of catheter 30, and a bidirectional deformation part 35 formed around slit 34. Bidirectional deformation part 35 is provided by forming oblique surfaces at the outside of parts opposed across slit 34 in catheter 30, such that sides defining slit 34 gradually become thin-walled. Bidirectional deformation part 35 forms a recess with a nearly triangular cross-sectional shape provided with two oblique surfaces projecting to the outside of the catheter 30.

Slit 34 is opened by deformation of the bidirectional deformation part 35 when the force applied perpendicular to bidirectional deformation part 35 reaches a predetermined value or higher, for example, 50-60 $cmH_2O$. If the force applied to bidirectional deformation part 35 is below a predetermined value, the elasticity of bidirectional deformation part 35 provides close contact of the confronting surfaces that form slit 34, and slit 34 is thereby closed. Bidirectional deformation part 35 can be formed in various ways; for example, once a tubular catheter with a closed end portion is formed, a heat gun or the like can be used on the tip portion thereof to apply an appropriately heated gas, thereby forming the oblique surfaces that include bidirectional deformation part 35.

Otherwise, an appropriately heated metal rod can be pressed against the tip-side portion of a tubular catheter with a closed tip portion to form the oblique surfaces that define bidirectional deformation part 35, or a tubular catheter with a closed tip portion can be covered with shrink tubing, and the oblique surfaces that define bidirectional deformation part 35 can be formed by shrinking a portion of such tubing. Bidirectional deformation part 35 may also be formed at the same time that a tubular catheter with a closed tip portion is formed. Slit 34 may be formed by cutting along the lengthwise direction in the center of bidirectional deformation part 35.

Figure 3:
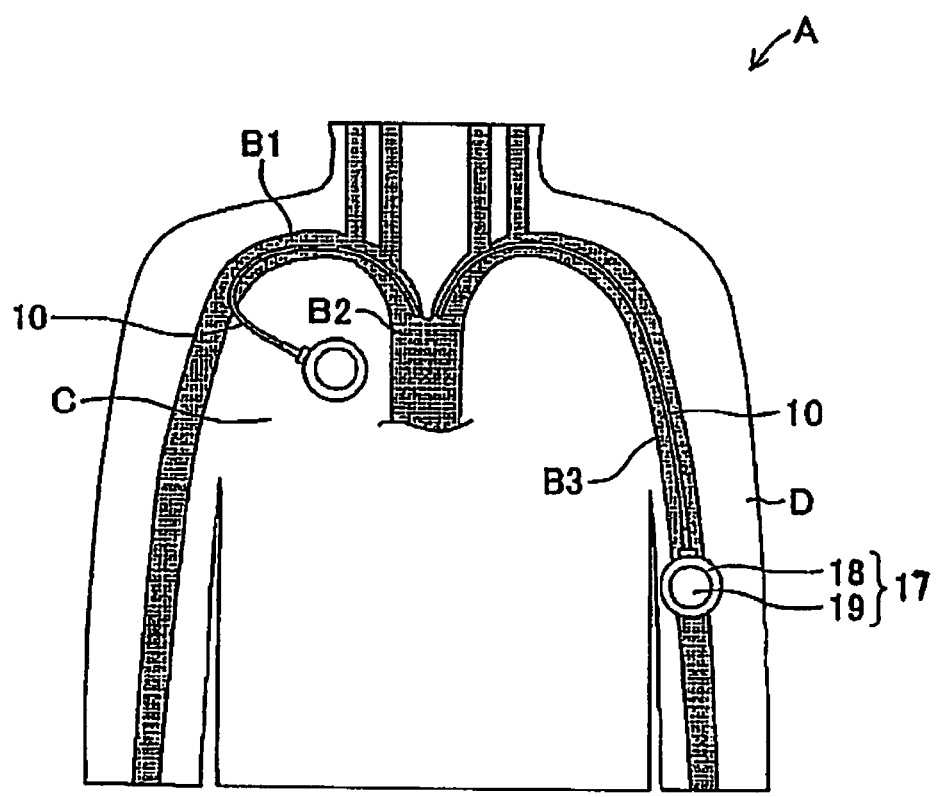
FIG. 3 is a descriptive view illustrating a catheter placed in the body of a patient.

With reference now to FIG. 3, when catheter 30 is used to supply a drug solution to the vein of a patient A, first, the port 17 is connected to the base terminal 11 of catheter 30. Port 17 is formed by a septum 19 attached to the surface of a circular, plate-shaped unit 18, forming an open space (not illustrated) in the interior. Septum 19 includes a material able to be pierced by a needle and endowed with the property that when the needle is withdrawn, the hole created by the needle is blocked. Consequently, when septum 19 in port 17 is pierced by the needle of a syringe filled with a drug solution, and the drug solution flows from the syringe into port 17, the drug solution passes from the space in port 17 into the interior of catheter 30 and flows outward from slit 34.

As shown in FIG. 3, catheter 30, to which port 17 is connected, may be inserted into a vein from the chest region C of patient A or inserted into a vein from an arm D of patient A. When catheter 30, with port 17 connected, is inserted from the chest region C into a vein, a region near a vein in chest region C, for example subclavian vein B1, is incised, catheter 30 is inserted from subclavian vein B1 located in the vicinity thereof, and the tip-side portion thereof reaches superior vena cava B2. Port 17 is then embedded beneath the chest skin.

When catheter 30 with port 17 attached is inserted into a vein from an arm D, the upper portion of arm D is incised, catheter 30 is inserted from brachial vein B3 located in the vicinity thereof, and the tip-side portion of catheter 30 reaches superior vena cava B2 from subclavian vein B1. Port 17 is then embedded beneath the chest skin. In either case, the interior of catheter 30 and port 17 are filled with physiological saline. The interior pressure and exterior pressure on catheter 30 are therefore nearly equal, and the closed status of slit 34 is maintained.

When a drug solution is supplied into the vein of patient A through catheter 30 with port 17 connected, the needle of a syringe filled with a drug solution is first inserted from the skin surface, septum 19 is pierced, and the tip of the needle is positioned within port 17. The drug solution is then infused from the syringe into port 17. The drug solution thus passes from the interior of port 17 into catheter 30 and enters superior vena cava B2 from slit 34. In this instance, the pressure applied to the drug solution by the syringe is greater than the pressure of blood within superior vena cava B2, bidirectional deformation part 35 is thereby easily deformed toward the outside of the catheter 30, and slit 34 is opened.

When blood is collected or a check is made for regurgitation, the needle of a syringe from which internal air has been expelled is inserted from the skin surface, and septum 19 is pierced. Then with the tip of the syringe located in port 17, the plunger of the syringe is withdrawn. Blood within the vein thus passes from the superior vena cava B2 through slit 34, and enters the interior of the catheter 30. In this instance, the suction force of the syringe easily deforms bidirectional deformation part 35 toward the interior of catheter 30, and slit 34 is opened. In this manner, slit 34 is easily opened both when a drug solution is supplied from the catheter 30 into a vein and when blood within a vein is withdrawn to the inside of the catheter 30, and the flow of the drug solution or blood is made smooth. When a drug solution is not being infused or blood is not being withdrawn by a syringe, the return force produced by the elasticity of bidirectional deformation part 35 also maintains slit 34 in closed status. Slit 34 opens easily not only when a drug solution flows from the inside toward the outside of the catheter, but also when blood flows from the outside toward the inside of the catheter 30, and the flow of a drug solution or blood can be made smooth.

Bidirectional deformation part 35 is deformed by additional pressure or reduced pressure derived from operation of a syringe, and slit 34 opens easily, but when blood flows from the outside toward the inside of catheter 30, the blood puts pressure on bidirectional deformation part 35 from the recess side, and slit 34 therefore opens even more easily. If the pressure differential between the inside and outside of catheter 30 is small, slit 34 is maintained in closed status by the elasticity of bidirectional deformation part 35. At such time, the opposing surfaces that form slit 34 in catheter 30 are in a state of contact with each other, and consequently there is no coagulation of blood within slit 34.

Figure 4:
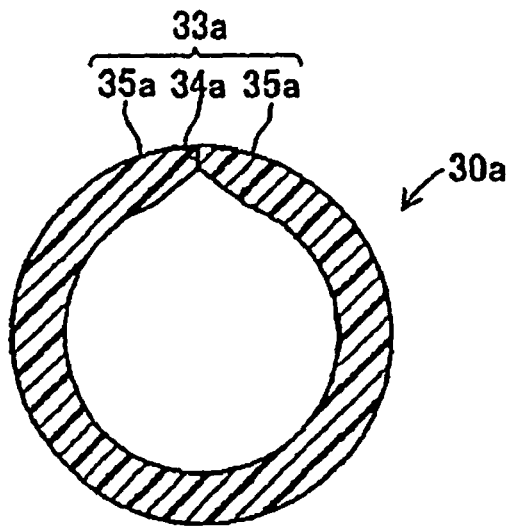
FIG. 4 is a cross-sectional view illustrating the tip-side portion of a catheter according to an alternative embodiment of the present disclosure.

With reference now to FIG. 4, the cross-section of the tip portion of a catheter 30a according to an alternative embodiment of the present disclosure is illustrated. Catheter 30a includes a bidirectional deformation part 35a of a valve 33a provided by forming oblique surfaces at the inner circumference of portions opposed across a slit 34a in catheter 30a, such that the sides defining slit 34a gradually become thin-walled. The structure of other portions of catheter 30a is identical to that of the catheter 30 described above.

When the catheter 30a is used to supply a drug solution into a vein of a patient A, the same procedure as described above can be performed, in which a catheter 30 was used to supply a drug solution into a vein of a patient A. As a result, when a drug solution flows from the inside toward the outside of the catheter, and when blood flows from the outside toward the inside of the catheter 30a, in either case, the slit 34a opens easily, and the flow of drug solution or blood toward its respective direction of orientation can be made smooth. The formation of oblique surfaces at the inner circumference adjacent slit 34a as in the catheter 30a allows the slit 34a to open more easily when a drug solution flows from the inside toward the outside of the catheter 30a. Other operational effects of the catheter 30a are similar to the operational effects of the catheter 30 described above.

Figure 5:
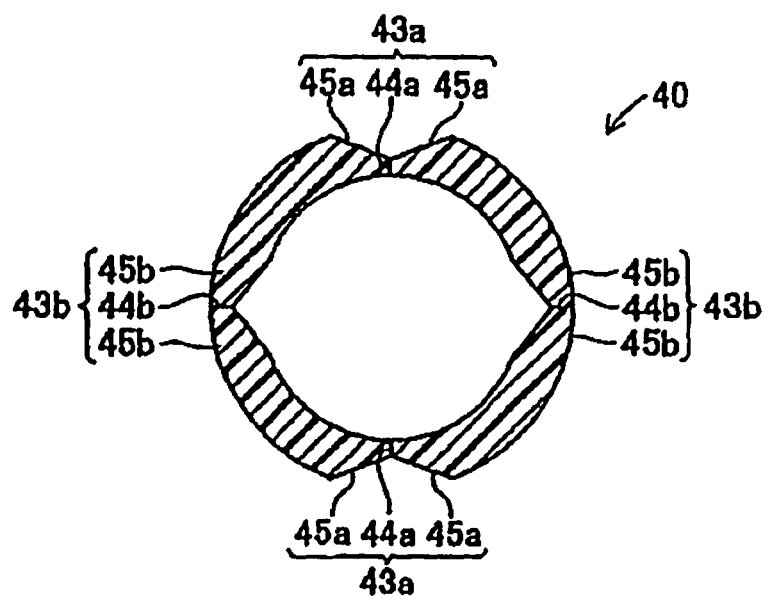
FIG. 5 is a cross-sectional view illustrating the tip-side portion of a catheter according to another embodiment of the present disclosure.

Turning now to FIG. 5, a cross-section of the tip-side portion of a catheter 40 according to another embodiment of the present disclosure is illustrated. Catheter 40 includes a plurality of valves 43a, 43b formed at regular intervals along the circumference. As shown, catheter 40 includes two (2) valves 43a and two (2) valves 43b disposed alternately about the circumference of catheter 40. Bidirectional deformation part 45a of valves 43a is provided by forming oblique surfaces at the outer circumference of portions opposed across the slit 44a in catheter 40 such that the sides defining slit 44a gradually become thin-walled. Bidirectional deformation part 45b of valve 43b is provided by forming oblique surfaces at the inner circumference of portions opposed across the slit 44b in catheter 40 such that the sides defining slit 44b gradually become thin-walled.

The structure of other portions of the catheter 40 is identical to that of the catheter 30 and others described above. When the catheter 40 is used to supply a drug solution into a vein of a patient A, the same procedure as described above may be performed, in which catheter 30 or others were used to supply a drug solution into a vein of a patient A. Accordingly, because a plurality of valves 43a, 43b is provided, infusion of a drug solution or collection of blood through the valves 43a, 43b can be performed more reliably. Additionally, due to this catheter with valve 40, if for example, one among the plurality of valves 43a, 43b becomes clogged, infusion of a drug solution or collection of blood through other of the valves 43a, 43b can still be performed.

When blood flows from the outside toward the inside of catheter 40, in either case, valves 43a open easily, and when a drug solution flows from the inside toward the outside of catheter 40, valves 43b open easily. As a result, when a drug solution flows from the inside toward the outside, and when blood flows from the outside toward the inside of catheter 40, in either case, the flow of drug solution or blood may be made smooth. Other operational effects of catheter 40 are similar to the operational effects of catheter 30 and others described above.

The catheters of the present disclosure are not limited to the individual embodiments described above and may be implemented with suitable modifications. For example, bidirectional deformation parts 35, 35a of catheters 30, 30a, respectively, are provided by forming oblique surfaces at the outer circumference or inner circumference of portions opposed across slit 34, 34a, such that the sides defining slits 34, 34a gradually become thin-walled; however, a bidirectional deformation part may also be provided by forming oblique surfaces at both the outer circumference and the inner circumference.

A bidirectional deformation part can also be provided by forming a groove-shaped, thin-walled portion at a portion maintaining a predetermined interval from slit 34 or others, and a bidirectional deformation part can also be provided by making the entire circumference of slit 34 or others thin-walled. The number of bidirectional deformation parts when a plurality is provided is also not limited to 4; 3 or fewer or 5 or more are also acceptable, and individual bidirectional deformation parts with shapes differing suitably can also be used in combination. A bidirectional deformation part may also be provided by making the part more flexible than other portions of a catheter. The outer circumferential portion of a slit may also be made into a bidirectional deformation part by making the inner space eccentric, such that the portion of a catheter with valve where a slit is provided gradually becomes thinner-walled than other portions.

In addition to a polyurethane resin, the material used to comprise catheter 30 or others described above may be a silicone, nylon, or a polyvinyl chloride. Additionally, in the embodiments described above, a port 17 is connected to a base terminal 11 of a catheter 30 or others, but the base terminal 11 of catheter 30 or others may also be connected to a transfusion line. As discussed above, catheter 30 or others was placed in a vein, but a predetermined method may also be used to place catheter 30 or others in an artery.

Although specific features of the catheter with valve are shown in some of the drawings and not in others, this is for convenience only as each feature may be combined with any or all of the other features in accordance with the aspects of the present disclosure. Other embodiments will occur to those skilled in the art and are within the following claims.

What is claimed is:

1. A catheter comprising:
   a tubular body having proximal and distal ends, and inner and outer surfaces;
   at least one valve formed near the distal end of the tubular body, the valve including a deformation portion defining a slit, the slit communicating from the inner surface to the outer surface of the tubular body, wherein the distance between the inner surface and the outer surface of the tubular body progressively thins within the deformation portion in a direction toward the slit, the deformation portion being deformable to open the slit in response to a force exerted on the deformation portion from the inner surface of the tubular body, and the deformation portion being deformable in response to a force exerted on the deformation portion from the outer surface of the tubular body.

2. The catheter of claim 1, wherein the deformation portion is deformable to open the slit in response to a perpendicular force exerted on the deformation portion from either the inner surface or the outer surface of the tubular body.

3. The catheter of claim 2, wherein the deformation portion is deformable to open the slit in response to a perpendicular force greater than 50 cm H2O.

4. The catheter of claim 1, wherein the slit is more easily opened in response to the force exerted on the deformation portion from the outer surface than in response to the force exerted on the deformation portion from the inner surface.

5. The catheter of claim 1, wherein the deformation portion includes an oblique surface defining the slit.

6. The catheter of claim 1, wherein a wall of the tubular body is thinnest about the slit.

7. The catheter of claim 1, wherein the slit extends along an axial direction defined by the tubular body.

8. The catheter of claim 1, wherein the deformation portion defines a recess with a nearly triangular cross-sectional shape.

9. The catheter of claim 1, wherein the at least one valve comprises two or more valves disposed at regular intervals along the circumference of the tubular body.

10. The catheter of claim 1, further comprising a dome-shaped wall portion at a tip of the tubular body, wherein the dome-shaped wall portion is softer than the tubular body.

11. A catheter comprising:
    a tubular body having proximal and distal ends, and inner and outer surfaces;
    at least one valve formed near the distal end of the tubular body, the valve including a deformation portion, the deformation portion including an oblique surface defining a slit, the deformation portion being deformable to open the slit in response to a force exerted on the deformation portion from the inner surface of the tubular body, and the deformation portion being deformable in response to a force exerted on the deformation portion from the outer surface of the tubular body.

12. The catheter of claim 11, wherein the oblique surface is formed at the outer surface of the tubular body.

13. The catheter of claim 11, wherein the slit is more easily opened in response to the force exerted on the deformation portion from the outer surface than in response the force exerted on the deformation portion from the inner surface.

14. The catheter of claim 11, wherein the at least one valve comprises two or more valves disposed at regular intervals along the circumference of the tubular body.

* * * * *